US005334135A

United States Patent [19]
Grim et al.

[11] Patent Number: 5,334,135
[45] Date of Patent: Aug. 2, 1994

[54] FORMED RESILIENT ORTHOPAEDIC SUPPORT

[76] Inventors: Tracy E. Grim, 3010 W. Boston Ct., Broken Arrow, Okla. 74012; Alec D. Bobroff, 12865 Glen Brae Dr., Saratoga, Calif. 95070

[21] Appl. No.: 18,004

[22] Filed: Feb. 16, 1993

[51] Int. Cl.⁵ .............................. A61F 5/00
[52] U.S. Cl. .............................. 602/26; 602/6; 602/13; 602/16; 602/20; 602/62; 2/22
[58] Field of Search .............. 602/26, 60, 61, 62, 602/77, 900, 901; 2/22, 24

[56] References Cited

U.S. PATENT DOCUMENTS

| | | |
|---|---|---|
| 3,587,572 | 6/1971 | Evans .............................. 602/26 |
| 4,632,106 | 12/1986 | Gamm . |
| 4,953,543 | 9/1990 | Grim et al. . |
| 4,993,409 | 2/1991 | Grim . |
| 5,026,339 | 6/1991 | Kasper . |
| 5,027,801 | 7/1991 | Grim . |
| 5,062,414 | 11/1991 | Grim . |
| 5,088,478 | 2/1992 | Grim .............................. 602/27 |

Primary Examiner—Richard J. Apley
Assistant Examiner—Beverly A. Meindl
Attorney, Agent, or Firm—Poms, Smith Lande & Rose

[57] ABSTRACT

An orthopaedic support includes a sheet of foam material that has been compression molded in specific areas. These areas have a thickness and density that is different from other areas of the support and serve to better fit the support to the body. The support may include compression molded grooves or cavities to accommodate straps, struts, gel-filled pads, inflatable bladders, pumps, and other accessories. The support may be compression molded into a shape that conforms to the general contour of the part of the human anatomy that it supports. The support may also include compression molded grooves that reduce bunching when the support is bent, and may include molded edges to minimize skin irritation during activity.

26 Claims, 3 Drawing Sheets

FORMED RESILIENT ORTHOPAEDIC SUPPORT

FIELD OF THE INVENTION

The present invention generally relates to orthopaedic supports for the human anatomy and, more particularly, to an orthopaedic support that is compression molded to improve the fit and performance of the support.

BACKGROUND OF THE INVENTION

Orthopaedic supports are typically used to stabilize and protect certain injured parts of the human anatomy. Such supports have often been used on knees, elbows, ankles, wrists, thighs and backs. These supports are intended to reduce strain on the injured body part, thereby allowing the injury to heal. Some supports have included struts and other hardware to help relieve some of the load from the injured part, and to restrict motion.

One such orthopaedic support is constructed as follows. First, the manufacturer cuts a base layer from a sheet of material, such as foam rubber. The manufacturer then sews a variety of pads onto the base layer, which may include buttresses, condylar pads, and popliteal pads. The manufacturer then sews on straps, which are used to secure the support to a limb. The manufacturer may also attach hardware to the support, or may sandwich such hardware between the base layer of material and a pad.

A number of problems arise with this common type of support. The first problem relates to the manufacturing process. To construct such a support, the manufacturer must cut the pads from a piece of material, position those pads onto the base layer, and sew the pads into place. The process of cutting, sewing, and positioning is labor-intensive and can become expensive. If a pad is improperly positioned and sewn, the entire support may need to be discarded as defective. Furthermore, material is wasted when the cutting process produces scrap pieces that must be thrown away.

A second set of problems arises with the support characteristics of this common type of orthopaedic support. First, the typical support stretches in order to roughly conform to the shape of joints and limbs. However, mere stretching cannot allow the support to closely conform to the nuances in the shape of the limb or joint, particularly in the case of knees, elbows and ankles. As a result, areas of the limb or joint are left under-supported or even entirely unsupported.

Another problem arises because the typical support has a base that is of uniform thickness and density, thereby producing uniform circumferential compression. Such compression cannot be increased or decreased to provide more or less support in selected areas of the injured limb or joint, in the absence of supplemental material straps. Consequently, such a support tends to shift position on the limb because there are no regions of high pressure to anchor it. Furthermore, a support having uniform thickness and density may allow the limb to move with equal ease in a variety of directions. Such ease of movement may increase the likelihood that a particular injury such as a patella injury will be aggravated.

A third set of problems arises with respect to the performance of the typical support. One problem is that the support material tends to bunch up whenever the limb is flexed. This bunching tends to interfere with the motion of the limb, is uncomfortable to the user, and may rub or chafe the skin and even bruise the skin. Another problem is that the edges of the typical support are die-cut, thereby exposing the user's skin to potentially allergenic support materials, such as neoprene. The edges tend to be rather rough, causing skin irritation during exercise.

An additional set of problems stems from hardware that may be attached to the typical support. Such hardware may include gel packs, inflatable bladders, pumps, straps, and struts. This hardware tends to protrude from the base of the support and can get caught on other objects. Since the hardware is typically sewn onto the base, the stitches can be ripped from the base and the hardware torn free. A special problem arises with hinged strut mechanisms, which can be twisted out of place so that the hinged strut does not properly guide and support the flexing motion of the joint.

SUMMARY OF THE INVENTION

There are a number of objects of the present invention. One object is to provide an orthopaedic support having varied thickness and material density. This support may be manufactured without having to cut and sew extra padding pieces. The varied thickness allows the manufacturer to increase or decrease the pressure provided to selected areas of the limb, including pressure that will prevent the support from shifting position. The varied density should allow the manufacturer to limit the range of limb motion in certain directions, Another important object of the present invention is to provide an orthopaedic support molded to generally conform to the contour of the part of the human anatomy that it supports. The edges may be shaped so that the skin is not exposed to allergenic or rough-edged material. The support should also not bunch up when a limb is flexed.

An additional object of the present invention is to provide an orthopaedic support having grooves to accommodate hardware. These grooves allow the hardware to remain close to the base of the support, maintain the proper position of the hardware, and act as hardware locators for ease of support assembly. Moreover, the grooves particularly act as locators for removable materials, and as gel pads, straps, etc., ensuring proper placement when re-attached.

Generally stated, an orthopaedic support that satisfies the foregoing objects includes a sheet of foam material, preferably foam rubber, that has been compression molded in specific areas. These areas have a thickness and density that is different from other areas of the support and which serve to better fit the support to the body. Such supports can be manufactured for use on various parts of the human anatomy.

Embodiments of the invention may include a number of features. The support may include compression molded grooves or cavities to accommodate straps, struts, gel-filled pads, inflatable bladders, pumps, and other accessories. The support may be compression molded into a shape that conforms to the general contour of the part of the human anatomy that it supports. The support may also include a number of compression molded grooves that reduce bunching when the support is bent. Edges of the support may have molded radii for minimizing skin irritation during activity.

One specific embodiment of the invention is a knee brace, which is manufactured from a sheet of foam rubber. The knee brace includes a front side to accommodate the patella and a rear popliteal side. Compression molded grooves extend across the popliteal side to reduce material bunching when the user bends her or his knee. The knee brace may also have a variety of compression molded pads and buttresses, as well as hardware and compression molded grooves and cavities to support that hardware.

As is apparent from the foregoing description, the present orthopaedic support readily satisfies the objects of the invention. The compression molded support is manufactured without having to cut and sew extra padding pieces. The variable thickness and density provide pressure to selected areas of a limb and improve the range of motion in certain directions. The shape of the support conforms to the contour of the part of the human anatomy that it supports, and the molded edges protect the user's skin from allergic reactions and abrasion. The compression molded grooves serve to prevent bunching of the material when the limb is flexed. Furthermore, other compression molded grooves accommodate hardware, act to maintain the hardware in proper position, and serve as hardware locators during assembly of the support.

Other objects, features, and advantages of the invention will become apparent from a consideration of the following detailed description and the accompanying drawings.

DETAILED DESCRIPTION OF PREFERRED EMBODIMENTS

Before considering a particular preferred embodiment, it is useful to discuss the invention in general. A principal characteristic of the present support invention is regions of varying thickness and density. These regions are created by a process known as compression molding, wherein a combination of heat and pressure is applied to a sheet of material. The manufacturer varies the amount of heat and pressure that is applied in different areas of the material in order to reduce thickness in certain areas. The areas that are not compressed, or which are only slightly compressed, can constitute regions of extra padding. The material is typically a closed-cell rubber, such as neoprene, although the material might also be a resilient open-cell material such as urethane foam.

The art of compression molding requires both special equipment and special skill. Therefore, a designer of a compression molded product will typically submit specifications to a commercial compression molding company, which will then manufacture the product. One such compression molding company is Rubatex Corporation of Bedford, Va.

Figure 10:
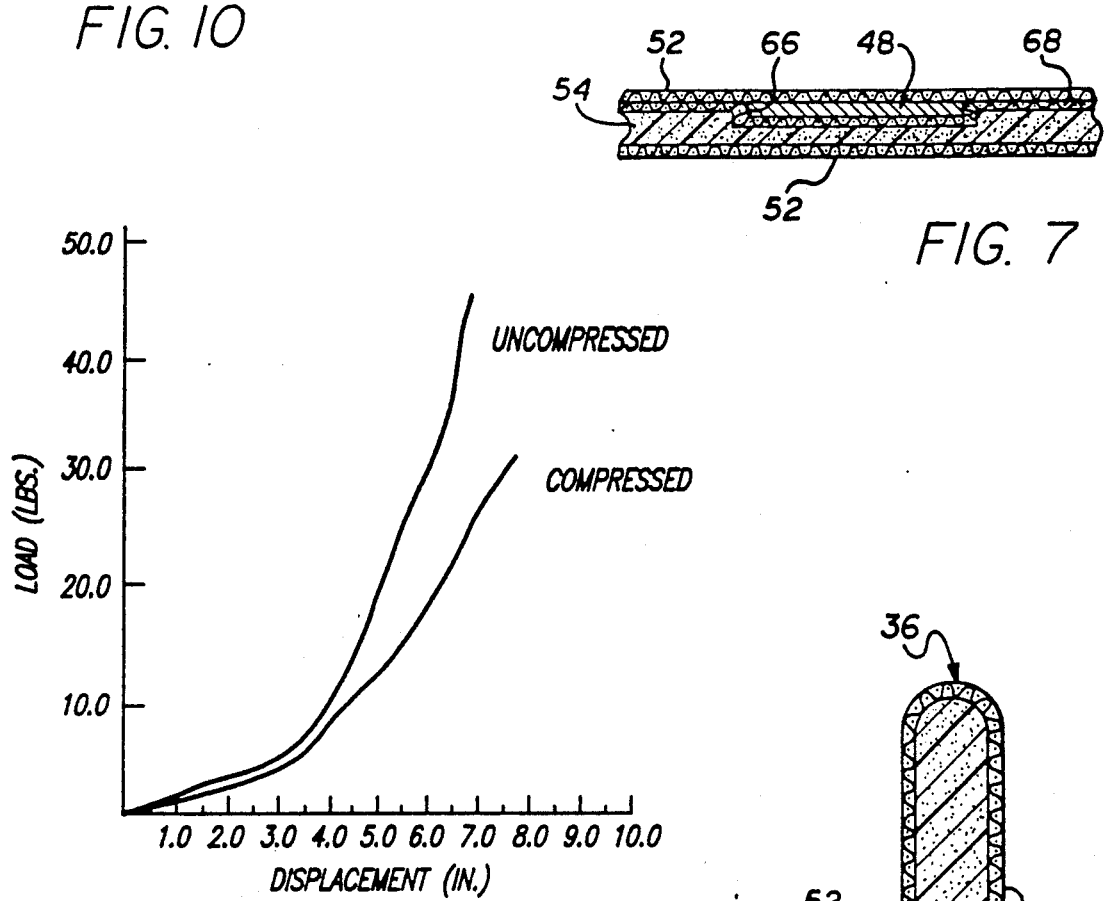
FIG. 10 is a comparison of the stretch characteristics of compressed and uncompressed foam rubber.

FIG. 10 is a comparison of the stretch characteristics of compressed and uncompressed foam rubber. This figure was derived from tension tests of uncompressed, and compressed samples of neoprene that were supplied to the inventors by the Rubatex Corporation. Each of the samples had a testing length of 3 inches and a width of 1 inch. The uncompressed samples were 3/16 inch thick, and the the compressed samples were ⅛ inch thick. As FIG. 10 illustrates, the compressed and uncompressed materials behave similarly at low loads. However, as the load increases, the compressed material tends to stretch more than the uncompressed material. By applying this principle to foam rubber orthopaedic support design, a designer may control the stretch characteristics of a support by varying the degree to which different regions of the support are compressed. Furthermore, because the support pressure of a foam rubber support is related to its stretch characteristics, the designer may simultaneously control the pressure that the brace exerts at different areas of an injured part of the human anatomy.

Figure 1:
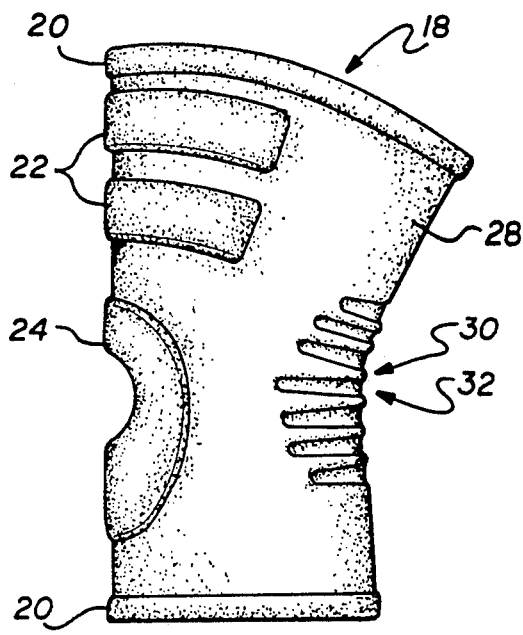
FIG. 1 is a side view of one embodiment of a formed foam rubber orthopaedic knee brace.

Now turning to one specific embodiment of the invention, FIG. 1 shows an orthopaedic knee brace 18. The brace has been compression molded to have a number of features. Strip pads 22 protect the flesh and muscle above the knee when the user either falls down or bumps into another object. Similar pads may be placed below the knee to protect the shin. Patellar buttress 24 supports and protects the patella. Main body 28 may be compression molded to have a generally uniform thickness and density, and therefore uniform stretch characteristics as may be desired for overall support.

Figure 2:
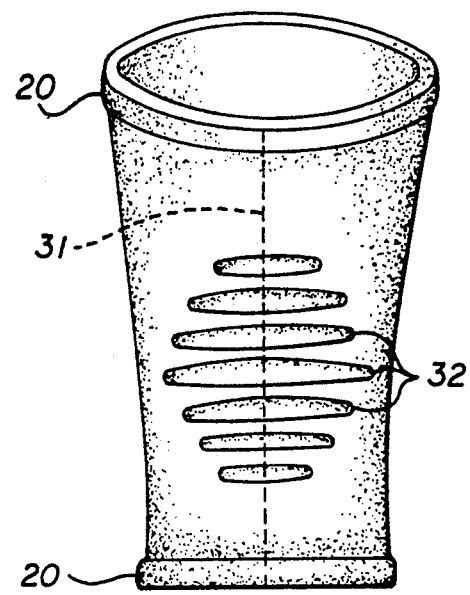
FIG. 2 is a rear perspective view of the formed foam rubber knee brace of FIG. 1.

The knee brace also includes compression molded transverse grooves 32 located in the rear popliteal area 30. These compression molded grooves 32 are shown in both FIGS. 1 and 2. Grooves 32 allow the rear popliteal area 30 to fold accordion style when the knee is bent. This feature overcomes the long standing problem of material bunching, which prevents the knee from flexing freely with traditional knee braces. Rear popliteal area 30 may have a generally relaxed thickness in order to help the knee bend. The sheet material is sewn together along sew line 31 as shown in FIG. 2.

Raised rims 20 act to anchor the knee brace onto the knee area. As discussed previously, and as shown in FIG. 10, compressed foam rubber stretches more easily than foam rubber that is not compressed or that is compressed relatively less. Consequently, rims 20 stretch relatively less than base 28, thereby causing rims 20 to behave like elastic bands around the portions of the leg that are above and below the knee. Thus, the knee brace of FIG. 1 is self-anchoring without the use of straps.

Figure 3:
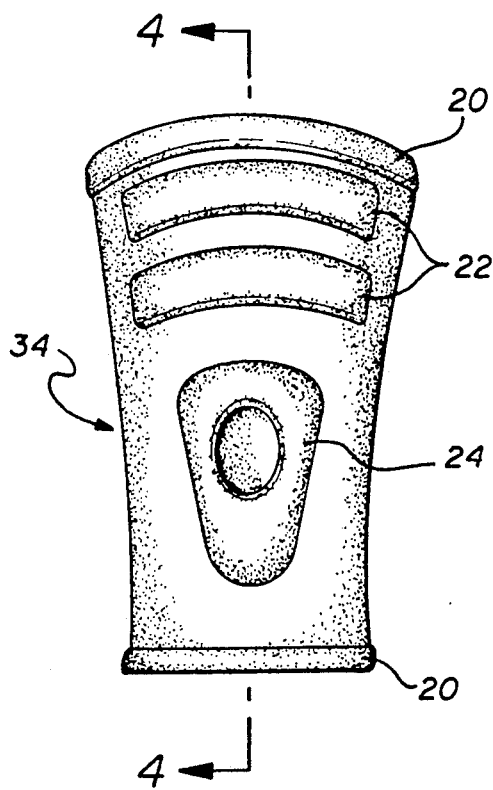
FIG. 3 is a front view of the formed foam rubber knee brace of FIG. 1.
Figure 4:
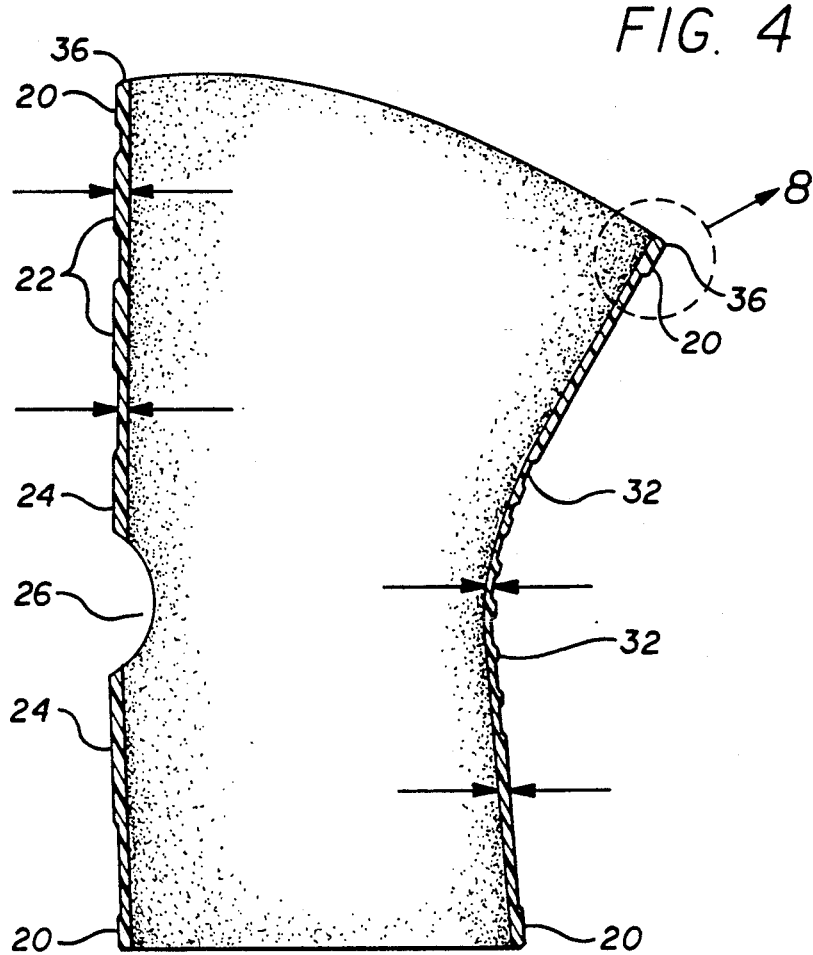
FIG. 4 is a sectional view of the formed foam rubber knee brace taken along the line 4—4 of FIG. 3.

The compression molded features of knee brace 18 are more particularly seen in FIG. 4, which is a cross sectional view of the brace taken at Section 4—4 of FIG. 3. FIG. 4 particularly shows such features as pads 22, patellar buttress 24, and transverse grooves 32. Also shown is patellar aperture 26, which allows the user to flex her or his knee with relative freedom. Note that the compression molding technique allows sudden discontinuities in height and density between raised and non-raised portions, thereby allowing the designer to create corresponding discontinuities in the pressure that the brace exerts on the limb.

Figure 8:
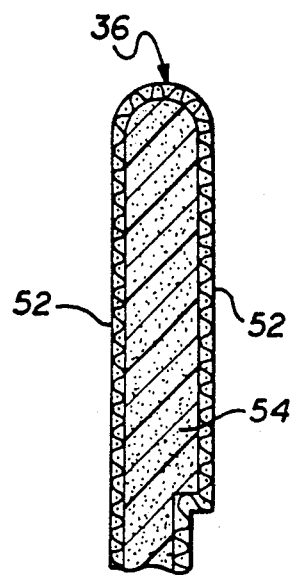
FIG. 8 is a close-up view of portion 8 of FIG. 4 showing a first outer layer of material, an inner layer of foam rubber, and a second outer layer of material.

FIG. 4 also illustrates molded edge 36, which rounds the interior of the edge away from the skin to reduce both allergy problems and irritation during exercise. FIG. 8, which is a close-up view of Section 8 of FIG. 4, shows a more detailed view of molded edge 36. FIG. 8 reveals that the knee brace 18 is formed from a material having three layers. The two outer layers 52 are typically a thin nylon or brushed nylon material. The middle layer 54 is typically a closed cell rubber such as neoprene. Molded edge 36 prevents the user's skin from coming into contact with middle layer 54, which is often allergenic. Furthermore, the skin does not come into contact with a rough edge, as it would if the edge was die cut.

Figure 5:
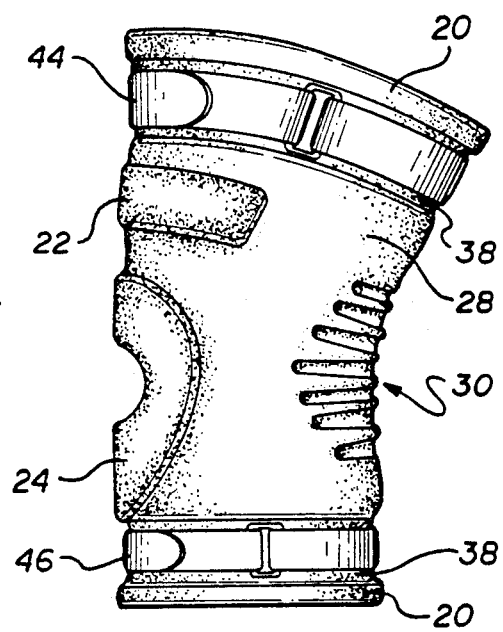
FIG. 5 is a side view of an embodiment of a formed foam rubber orthopaedic knee brace having grooves for straps.

FIG. 3 illustrates the overall appearance of the leg and knee brace 34. Several types of channels, grooves, and indentations can be compression molded into the brace. These channels and indentations serve to hold brace hardware into place, to prevent the hardware from protruding from the brace, and to serve as hardware locators during the manufacturing process. The strap grooves 38 are an example of this type of compression molded groove, as shown in FIG. 5. The strap grooves guide or maintain straps 44 and 46 in place so that there may be no need to sew the straps onto the brace itself. Note that the level of the straps is about even with base 28 of the brace, and the straps do not protrude. Thus, it is unlikely that the straps will catch on external objects when the brace is worn.

Figure 6:
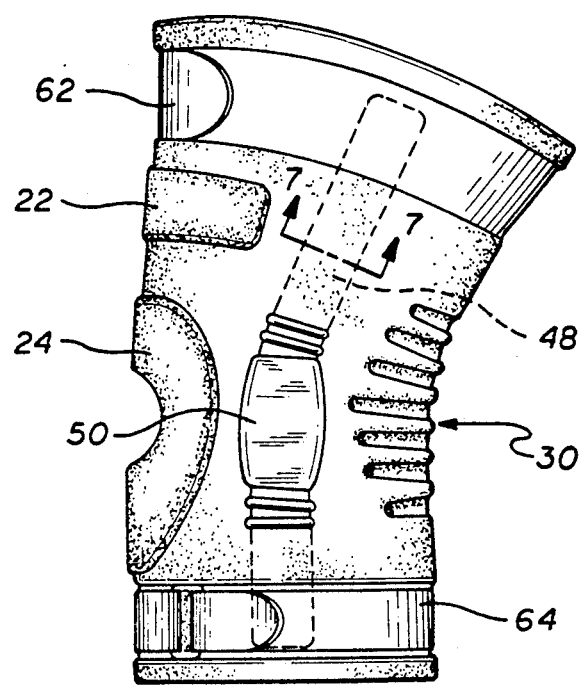
FIG. 6 is a side view of an embodiment of a formed foam rubber orthopaedic knee brace having grooves for struts and for straps.
Figure 7:
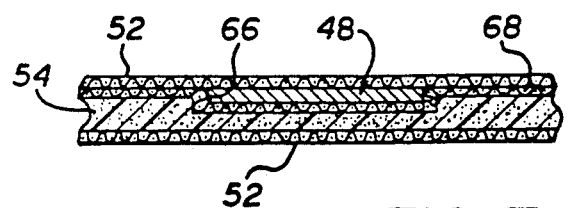
FIG. 7 is a cross-sectional view taken along line 7—7 of FIG. 6 showing the strut and the strut groove.

FIG. 6 illustrates a knee brace having a compression molded channel for strut and hinge hardware, which serve to reduce the load that bears directly on the knee. The compression molded channel holds strut 48 and strut hinge 50 in place, and prevents strut 48 and strut hinge 50 from significantly protruding from the brace. FIG. 7, which is a cross sectional view taken along Section 7—7 of FIG. 6, shows strut 48 neatly resting inside strut channel 66. Strut 48 is covered by one of two outer layers 52, which are typically a nylon or brushed nylon material. A second layer 68 of the same material lies underneath outer layer 52 and underneath strut 48. The base of the brace is an inner layer of material 54, which is typically foam rubber. Outer layer 52 lies flat over strut 48, such that the strut itself is not visible from the exterior of the brace. These strut channels 66 allow strut 48 to rest underneath straps 62 and 64, thereby allowing the user to secure the brace to her or his knee without interference from the strut mechanism.

Figure 9:
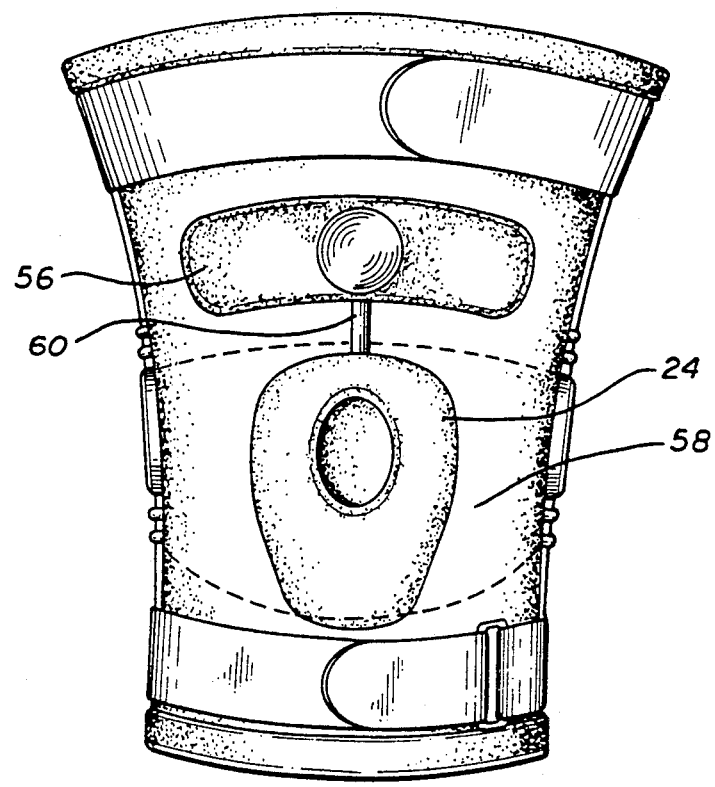
FIG. 9 is a front view of an embodiment of a formed foam rubber orthopaedic knee brace having grooves for a bladder, a pump, and a tube connecting the pump to the bladder.

FIG. 9 illustrates an air bladder, an associated air pump, and a tube to connect the air pump to the air bladder, all of which rest neatly inside compression molded indentations. The bladder 58 serves to support and protect the knee beyond what patellar buttress 24 can provide. Tube 60 connects pump 56 to bladder 58. The user may pump more or less air into the bladder to adjust the pressure that the bladder exerts upon the knee. Such air packs weigh very little, yet can add considerable support to the knee.

Similar channels and indentations can be compression molded into the brace for a variety of other types of hardware. For instance, indentations can be provided for gel packs, which are used either to protect against impact and/or for thermal therapy. A gel pack for protecting against impact may be permanently located underneath the surface of the knee brace, similar to the manner in which strut 48 is permanently buried underneath the surface of the knee brace in FIG. 7. Gel packs that are to be used for thermal therapy must be removable, and may rest inside a pouch partially defined by a compression molded indentation. In the case of heat therapy, the user first heats a gel pack, then inserts the gel pack into a gel pack pouch. Once the gel pack has cooled somewhat, the user replaces it with a freshly heated gel pack.

The following dimensions are provided by way of example and not of limitation. Referring to FIG. 1, the foam rubber sheet has an uncompressed thickness of 3/16". Pads 22, rims 20 and patellar buttress 24 are not compressed and have the same 3/16" thickness. Base 28 is compression molded to a thickness of ⅛". Transverse grooves 32 have a thickness of 1/16". Of course, numerous variations are possible. One such variation is to reduce the thickness of the entire popliteal area 30, thereby allowing the user to bend her or his knee more easily.

It should be noted that knee brace 18 is presented as just one of a multitude of possible embodiments of the invention. The invention encompasses a wide range of compression molded supports and braces for all other parts of the body. Thus, in addition to knee braces, the invention includes similar supports for elbows, thighs, wrists, ankles, backs, feet, and shins.

In conclusion, it is to be understood that the foregoing detailed description and the accompanying drawings relate to preferred embodiments of the invention. Various changes and modifications may be made without departing from the spirit and scope of the invention. Thus, by way of example and not of limitation, the material need not be nylon-covered neoprene, but could be another closed cell rubber, or an open cell foam such as urethane. The pads could be positioned in various places, such as below the knee to protect the tibial spine, tibial crest and tibial tubercle during a fall. The thickness of the base can be patterned to make the brace stretch more easily in certain directions than in other directions, and the stretch characteristics may be custom designed for particular injuries. The straps could be replaced with bands of a strong elastic material, which could be covered with nylon to make them invisible from the exterior. The patellar buttresses could have a different shape or could be substantially larger than that shown in the drawings. Air pump 56 can be located in a variety of places. Similarly, the air pump can be an external unit that temporarily connects to the bladder to fill the bladder with air. Additionally, compression molded transverse grooves 32 may not exist in some embodiments where ease of bending is not desired. Instead, some knee braces may have a rigid member along rear popliteal side 30 to prevent any bending of the knee whatsoever. Similar modifications may be made to the multitude of other embodiments of the present invention. Accordingly, the present invention is not limited to the specific embodiments shown in the drawings and described in the detailed description.

We claim:
1. An orthopaedic knee brace comprising:
   foam rubber sheet material for extending around the knee area;

means for orienting the knee brace with a front side accommodating the patella and a rear popliteal side;

said popliteal side being provided with a plurality of compression molded, substantially transverse, linearly extending grooves of reduced thickness, constituting means for reducing bunching of the knee brace when the leg is bent at the knee; and said foam rubber sheet material having a surface and a predetermined thickness in major areas of said brace away from the ribbed area on the rear of the knee brace opposite the patella, said grooves extending inward from said surface, and the thickness of said brace at the bottom of said grooves being substantially less than said predetermined thickness.

2. An orthopaedic knee brace as defined in claim 1, wherein the knee brace further comprises straps for securing the knee brace, and one or more compression molded strap grooves to accommodate the straps.

3. An orthopaedic knee brace as defined in claim 1, wherein the knee brace further comprises strut means for additional limb support and compression molded grooves to receive the strut means.

4. An orthopaedic knee brace as defined in claim 1, wherein the knee brace further comprises an integral, raised patellar buttress portion on said front side for providing additional support and protection for the patella.

5. An orthopaedic knee brace as defined in claim 1, wherein the knee brace further comprises gel-filled pads and one or more compression molded cavities to accommodate the gel-filled pads.

6. An orthopaedic knee brace as defined in claim 1, wherein the knee brace further comprises an inflatable bladder, a compression molded cavity to accommodate the bladder, and a pump for inflating the bladder.

7. An orthopaedic knee brace as defined in claim 1, wherein the knee brace further comprises a plurality of integral regions, some of said regions having a thickness and density that is different from one or more other regions, for the purpose of providing additional support or padding in some of the regions.

8. An orthopaedic knee brace as defined in claim 1, wherein the foam rubber sheet comprises a thin outer layer of nylon, a thin inner layer of nylon, and a layer of neoprene in between said inner and outer layers.

9. An orthopaedic knee brace as defined in claim 1 including a compression molded area extending around the knee brace, and an uncompressed ring of said foam rubber sheet material extending around the knee brace at upper and lower edges of said knee brace, said uncompressed rings being substantially thicker than said compression molded area.

10. An orthopaedic support comprising:
means for supporting a portion of the anatomy;
foam material in sheet form constituting at least a part of said support;
said foam material being molded in specific areas to vary the thickness and density of the material to improve the function of said support; and
said foam rubber sheet material having a surface, a predetermined thickness in major areas of said support, and grooves extending inward from said surface, the thickness of said brace at the bottom of said grooves being substantially less than said predetermined thickness.

11. The orthopaedic support as defined in claim 10, wherein the support further comprises straps for securing the support, and one or more compression molded strap grooves to accommodate said straps.

12. The orthopaedic support as defined in claim 10, wherein the support further comprises strut means for additional limb support and compression molded grooves to receive said strut means.

13. The orthopaedic support as defined in claim 10, wherein the support further comprises gel-filled pads and one or more compression molded cavities to accommodate said gel-filled pads.

14. The orthopaedic support as defined in claim 10, wherein the support further comprises an inflatable bladder, one or more cavities to accommodate said inflatable bladder, and a pump for inflating the bladder.

15. The orthopaedic support as defined in claim 10, wherein the support further comprises compression molded edges for minimizing skin irritation during activity.

16. The orthopaedic support as defined in claim 10, wherein the support is compression molded into a shape that conforms to the general contour of the portion of the human anatomy that it supports.

17. The orthopaedic support as defined in claim 10, wherein the foam rubber sheet comprises a thin outer layer of nylon, a thin inner layer of nylon, and a layer of neoprene in between said inner and outer layers.

18. The orthopaedic support as defined in claim 10, wherein said support comprises a plurality of compression molded, transverse, linearly extending grooves of reduced thickness, constituting means for reducing bunching of the support when the support is bent.

19. An orthopaedic support comprising:
means for supporting a portion of the anatomy;
foam material in sheet form constituting at least a part of said support;
said foam material in sheet form being molded in specific areas to vary the thickness and density of the material to improve the function of said support; and
said support including areas subject to greater flexing in a first area in the immediate vicinity of said joint and lesser flexing at other areas away from the immediate vicinity of said joint, said foam material being compressed in said first area to be generally thinner and to give greater flexibility and resiliency, and being substantially thicker in said other areas.

20. An orthopaedic support as defined in claim 19, wherein the orthopaedic support further comprises straps for securing the support, and one or more compression molded strap grooves to accommodate said straps.

21. An orthopaedic support as defined in claim 19, wherein the orthopaedic support further comprises strut means for additional limb support, and compression molded grooves to receive said strut means.

22. An orthopaedic support comprising:
means for supporting a portion of the anatomy;
foam material in sheet form constituting at least a part of said support;
said foam material being molded in specific areas to vary the thickness and density of the material to improve the function of said support;
said support including areas subject to greater flexing in a first area and lesser flexing at other areas, said foam material being varied in thickness to give greater flexibility and resiliency in said first area than in said other areas; and said foam rubber sheet material having a surface, a predetermined thickness in major areas of said support, and grooves extending inward from said surface, the thickness of said brace at the bottom of said grooves being substantially less than said predetermined thickness.

23. An orthopaedic knee brace comprising:

foam rubber sheet material for extending around the knee area; means for orienting the knee brace with a front side accommodating the patella and a rear popliteal side; and said popliteal side being provided with a plurality of compression molded, substantially transverse, linearly extending grooves of reduced thickness, constituting means for reducing bunching of the knee brace when the leg is bent at the knee; and said front side having an aperture to allow a user to flex her or his knee with relative freedom.

24. An orthopaedic knee brace comprising:

foam rubber sheet material for extending around the knee area; means for orienting the knee brace with a front side accommodating the patella and a rear popliteal side; and said popliteal side being provided with a plurality of compression molded, substantially transverse, linearly extending grooves of reduced thickness, constituting means for reducing bunching of the knee brace when the leg is bent at the knee; and the knee brace further comprising compression molded edges for minimizing skin irritation during activity.

25. An orthopaedic support comprising:

means for supporting a portion of the anatomy;

foam material in sheet form constituting at least a part of said support;

said foam material being molded in specific areas to vary the thickness and density of the material to improve the function of said support; and said foam material being foam rubber.

26. An orthopaedic knee brace comprising:

foam rubber sheet material for extending around the knee area;

means for orienting the knee brace with a front side accommodating the patella and a rear popliteal side;

said popliteal side being provided with a plurality of compression molded, substantially transverse, linearly extending grooves of reduced thickness, constituting means for reducing bunching of the knee brace when the leg is bent at the knee; and said knee brace being compression molded into a shape that conforms to the general contour of the leg and the knee.

* * * * *